United States Patent
Way et al.

(10) Patent No.: US 9,687,323 B2
(45) Date of Patent: Jun. 27, 2017

(54) TEMPORARY ANCHORAGE DEVICE WITH EXTERNAL PLATE

(71) Applicant: Propel Orthodontics, LLC, Ossining, NY (US)

(72) Inventors: Bryce A. Way, San Jose, CA (US); Mani Alikhani, New York, NY (US); Christopher U. Phan, San Leandro, CA (US)

(73) Assignee: Propel Orthodontics, LLC, Ossining, NY (US)

( * ) Notice: Subject to any disclaimer, the term of this patent is extended or adjusted under 35 U.S.C. 154(b) by 204 days.

(21) Appl. No.: 14/401,562

(22) PCT Filed: Jun. 6, 2013

(86) PCT No.: PCT/US2013/044567
§ 371 (c)(1),
(2) Date: Nov. 17, 2014

(87) PCT Pub. No.: WO2013/184948
PCT Pub. Date: Dec. 12, 2013

(65) Prior Publication Data
US 2015/0320523 A1     Nov. 12, 2015

Related U.S. Application Data (60) Provisional application No. 61/656,776, filed on Jun. 7, 2012.

(51) Int. Cl.
*A61C 7/00* (2006.01)
*A61C 8/00* (2006.01)
*A61C 7/12* (2006.01)

(52) U.S. Cl.
CPC .............. *A61C 8/0096* (2013.01); *A61C 7/12* (2013.01)

(58) Field of Classification Search
CPC ............ A61C 7/00; A61C 7/12; A61C 8/0096
See application file for complete search history.

(56) References Cited

U.S. PATENT DOCUMENTS 430,299 A    6/1890   Rand
D88,859 S    1/1933   Curtis
(Continued)

FOREIGN PATENT DOCUMENTS

CA    2406986 A1    4/2004
CN    2209958 Y    10/1995
(Continued)

OTHER PUBLICATIONS

Adachi et al; Enhancement of cytokine production by macrophages stimulated with (1-->3)-beta-D-glucan, grifolan (GRN), isolated from Grifola frondosa; Biol Pharm Bull; 17(12):1554-60; Dec. 1994.

(Continued)

*Primary Examiner* — Glenn Richman
(74) *Attorney, Agent, or Firm* — Shay Glenn LLP

(57) ABSTRACT

A temporary anchor device includes at least one screw mechanism and an external plate. The at least one screw mechanism includes a skeletal screw having a threaded portion configured to drill into jaw bone of a patient, a smooth portion configured to sit within gums of the patient, and a proximal portion configured to extend external to the gums. The at least one screw mechanism further includes an attachment mechanism configured to attach to the proximal portion of the skeletal screw. The external plate is configured to be locked between the skeletal screw and the attachment mechanism to anchor the external plate external to the gums.

18 Claims, 6 Drawing Sheets

(56) References Cited

U.S. PATENT DOCUMENTS

| | | | |
|---|---|---|---|
| 2,390,309 A | 12/1945 | Keys | |
| 2,564,356 A | 8/1951 | Dianda | |
| 3,360,861 A | 1/1968 | Hoffman | |
| 3,682,177 A | 8/1972 | Ames et al. | |
| 3,838,517 A | 10/1974 | Michnick | |
| 4,123,844 A | 11/1978 | Kurz | |
| 4,347,054 A | 8/1982 | Kraus et al. | |
| D266,109 S | 9/1982 | Sertich et al. | |
| 4,354,832 A | 10/1982 | Wallshein | |
| 4,433,956 A | 2/1984 | Witzig | |
| 4,482,318 A | 11/1984 | Foerster | |
| 4,483,674 A | 11/1984 | Schuetz | |
| 4,549,538 A | 10/1985 | Schadrack et al. | |
| D285,835 S | 9/1986 | Hanses | |
| 4,747,824 A | 5/1988 | Spinello | |
| 4,777,852 A | 10/1988 | Herman et al. | |
| 4,828,113 A | 5/1989 | Friedland et al. | |
| 4,944,677 A | 7/1990 | Alexandre | |
| 5,002,485 A | 3/1991 | Aagesen | |
| 5,030,098 A | 7/1991 | Branford | |
| 5,173,050 A | 12/1992 | Dillon | |
| 5,188,531 A | 2/1993 | Von Sutfin | |
| 5,191,880 A | 3/1993 | McLeod et al. | |
| 5,281,133 A | 1/1994 | Farzin-Nia | |
| 5,320,532 A | 6/1994 | Farzin-Nia et al. | |
| 5,343,883 A | 9/1994 | Murayama | |
| 5,351,404 A | 10/1994 | Smith | |
| 5,439,377 A | 8/1995 | Milanovich | |
| 5,472,344 A | 12/1995 | Binder et al. | |
| 5,547,657 A | 8/1996 | Singleton et al. | |
| D379,750 S | 6/1997 | Thompson et al. | |
| 5,676,682 A | 10/1997 | Yoon | |
| 5,957,946 A | 9/1999 | Shuler et al. | |
| 5,961,535 A | 10/1999 | Rosenberg et al. | |
| 6,019,776 A | 2/2000 | Preissman et al. | |
| 6,032,677 A | 3/2000 | Blechman et al. | |
| 6,106,289 A | 8/2000 | Rainey et al. | |
| 6,109,916 A | 8/2000 | Wilcko et al. | |
| D440,479 S | 4/2001 | Hsiao | |
| 6,234,975 B1 | 5/2001 | McLeod et al. | |
| D454,767 S | 3/2002 | Edwards | |
| 6,543,315 B2 | 4/2003 | Huang | |
| 6,592,368 B1 | 7/2003 | Weathers, Jr. | |
| 6,648,639 B2 | 11/2003 | Mao | |
| 6,652,473 B2 | 11/2003 | Kaufman et al. | |
| 6,739,872 B1 | 5/2004 | Turri | |
| 7,166,067 B2 | 1/2007 | Talish et al. | |
| D547,868 S | 7/2007 | Nakanishi | |
| 7,258,694 B1 | 8/2007 | Choi et al. | |
| 7,322,948 B2 | 1/2008 | Talish et al. | |
| 7,329,121 B2 | 2/2008 | De Clerck | |
| 7,329,122 B1 | 2/2008 | Scott | |
| 7,338,494 B2 | 3/2008 | Ryan | |
| 7,347,687 B2 | 3/2008 | Minoretti et al. | |
| 7,419,680 B2 | 9/2008 | LeGeros | |
| 7,462,158 B2 | 12/2008 | Mor | |
| 7,611,355 B2 | 11/2009 | Murias | |
| 7,618,450 B2 | 11/2009 | Zarowski et al. | |
| D607,300 S | 1/2010 | Lin | |
| D616,278 S | 5/2010 | Deguglimo et al. | |
| D628,697 S | 12/2010 | Murias | |
| D629,102 S | 12/2010 | Murias et al. | |
| D644,910 S | 9/2011 | Hsu | |
| D662,206 S | 6/2012 | Way et al. | |
| D668,339 S | 10/2012 | Luoto | |
| 8,602,777 B2 | 12/2013 | Way et al. | |
| D700,330 S | 2/2014 | Way et al. | |
| 8,770,969 B2 | 7/2014 | Way et al. | |
| 9,131,992 B2 * | 9/2015 | Itsuki | A61C 7/00 |
| 2006/0116581 A1 | 6/2006 | Zdeblick et al. | |
| 2006/0281040 A1 | 12/2006 | Kelling | |
| 2007/0298375 A1 | 12/2007 | Hirsch et al. | |
| 2008/0227046 A1 | 9/2008 | Lowe et al. | |
| 2008/0233541 A1 | 9/2008 | De Vreese et al. | |
| 2009/0035727 A1 | 2/2009 | Maissami | |
| 2009/0042159 A1 | 2/2009 | Yamamoto et al. | |
| 2009/0061375 A1 | 3/2009 | Yamamoto et al. | |
| 2009/0061379 A1 | 3/2009 | Yamamoto et al. | |
| 2009/0061380 A1 | 3/2009 | Yamamoto et al. | |
| 2009/0068285 A1 | 3/2009 | LeGeros et al. | |
| 2009/0275954 A1 | 11/2009 | Phan et al. | |
| 2009/0326602 A1 | 12/2009 | Glukhovsky et al. | |
| 2010/0055634 A1 | 3/2010 | Spaulding et al. | |
| 2010/0092916 A1 | 4/2010 | Teixeira et al. | |
| 2010/0136504 A1 | 6/2010 | Sabilla | |
| 2010/0266983 A1 | 10/2010 | Ng et al. | |
| 2011/0045435 A1 | 2/2011 | Goodman | |
| 2011/0065060 A1 | 3/2011 | Teixeira et al. | |
| 2011/0207075 A1 | 8/2011 | Altshuler et al. | |
| 2012/0094246 A1 | 4/2012 | Pavlin | |
| 2012/0179070 A1 | 7/2012 | Pommer et al. | |
| 2012/0322018 A1 | 12/2012 | Lowe et al. | |
| 2014/0322663 A1 | 10/2014 | Way et al. | |
| 2016/0317255 A1 | 11/2016 | Way et al. | |

FOREIGN PATENT DOCUMENTS

| | | |
|---|---|---|
| CN | 2266999 Y | 11/1997 |
| CN | 1359277 A | 7/2002 |
| CN | 1371663 A | 10/2002 |
| CN | 101262831 A | 9/2008 |
| CN | 201179118 Y | 1/2009 |
| CN | 201200485 Y | 3/2009 |
| CN | 202028800 U | 11/2011 |
| CN | 202113173 U | 1/2012 |
| CN | 202277392 U | 6/2012 |
| CN | 102908198 A | 2/2013 |
| CN | 102935014 A | 2/2013 |
| CN | 202843827 U | 4/2013 |
| CN | 202908860 U | 5/2013 |
| CN | 103249372 A | 8/2013 |
| CN | 103271773 A | 9/2013 |
| CN | 203303172 U | 11/2013 |
| EP | 0531950 A1 | 3/1993 |
| EP | 1535586 A2 | 6/2005 |
| JP | 2007097987 A | 4/2007 |
| JP | 2009000412 A | 1/2009 |
| KR | 20030066288 A | 8/2003 |
| RU | 2223056 C2 | 2/2004 |
| WO | WO 2006/070957 A1 | 7/2006 |
| WO | WO 2007/047983 A2 | 4/2007 |
| WO | WO 2007/140579 A1 | 12/2007 |
| WO | WO 2009/088165 A1 | 7/2009 |

OTHER PUBLICATIONS

Alhashimi et al; Orthodontic movement induces high numbers of cells expressing IFN-gamma at mRNA and protein levels; J Interferon Cytokine Res; 20(1):7-12; Jan. 2000.

Anholm et al; Corticotomy-facilitated orthodontics; CDA J; 14(12):7-11; Dec. 1986.

Arend et al.; IL-1, IL-18, and IL-33 families of cytokines; Immunol Rev; 223:20-38; Jun. 2008.

Arias et al.; Aspirin, acetaminophen, and ibuprofen: their effects on orthodontic tooth movement; Am J Orthod Dentofacial Orthop; 130(3):364-370; Sep. 2006.

Bai et al.; Interleukin-18 gene polymorphisms and haplotypes in patients with oral lichen planus: a study in an ethnic Chinese cohort; Tissue Antigens; 70(5):390-397; Nov. 2007.

Basaran et al.; Interleukins 2, 6, and 8 levels in human gingival sulcus during orthodontic treatment; Am J Orthod Dentofacial Orthop; 130(1):7.e1-6; Jul. 2006.

Bishara et al.; Maxillary expansion: clinical implications; 91(1):3-14; Jan. 1987.

Bolander; Regulation of fracture repair by growth factors; Proc Soc Exp Biol Med; 200(2):165-170; Jun. 1992.

Bossù et al; Interleukin 18 gene polymorphisms predict risk and outcome of Alzheimer's disease; J Neurol Neurosurg Psychiatry; 78(8):807-811; Aug. 2007 (Author's Manuscript).

Busti et al.; Effects of perioperative antiinflammatory and immunomodulating therapy on surgical wound healing; Pharmacotherapy; 25(11):1566-1591; Nov. 2005.

(56) References Cited

OTHER PUBLICATIONS

Chao et al.; Effects of prostaglandin E2 on alveolar bone resorption during orthodontic tooth movement; Acta Anat (Basel); 132(4):304-309; Jul. 1988.
Chung et al.; Corticotomy-assisted orthodontics; J Clin Orthod; 35(5):331-339; May 2001.
Davidovitch et al.; Neurotransmitters, cytokines, and the control of alveolar bone remodeling in orthodontics; Dent Clin North Am; 32(3):411-435; Jul. 1988.
De Sá et al.; Immunolocalization of interleukin 4, interleukin 6, and lymphotoxin alpha in dental granulomas; Oral Surg Oral Med Oral Pathol Oral Radiol Endod; 96(3):356-60; Sep. 2003.
Dienz et al.; The effects of IL-6 on CD4 T cell responses; Clin Immunol; 130(1):27-33; Jan. 2009 (Author's Manuscript).
Erben; Embedding of bone samples in methylmethacrylate: an improved method suitable for bone histomorphometry, histochemistry, and immunohistochemistry; J Histochem Cytochem; 45(2):307-313; Feb. 1997.
Fischer; Orthodontic treatment acceleration with corticotomy-assisted exposure of palatally impacted canines; Angle Orthod; 77(3):417-420; May 2007.
Foster; Principals of removable appliance treatment; in A Textbook of Orthodontics; 2nd Ed.; Blackwell Sci. Pub.; Chap. 13; pp. 246-261; Nov. 1975.
Frost; A Synchronous Group of Mammalian Cells Whose In Vivo Behavior Can be Studied; H Ford Hosp Med Bull; 13:161-172; Jun. 1965.
Frost; Part 1. The biology of fracture healing. An overview for clinicians; Clin Orthop Relat Res; 248:283-293; Nov. 1989.
Frost; Part II. The biology of fracture healing. An overview for clinicians; Clin Orthop Relat Res; 248:294-309; Nov. 1989.
Frost; The regional acceleratory phenomenon: a review; H Ford Hosp Med J; 31(1):3-9; (year of pub. sufficiently earlier than effective US filed and any foreign priority date) 1983.
Gantes et al.; Effects on the periodontium following corticotomy-facilitated orthodontics. Case reports; J Periodontol; 61(4):234-238; Apr. 1990.
Garlet et al.; Cytokine expression pattern in compression and tension sides of the periodontal ligament during orthodontic tooth movement in humans; Eur J Oral Sci; 115(5):355-62; Oct. 2007.
Germeç et al.; Lower incisor retraction with a modified corticotomy; Angle Orthod; 76(5):882-890; Sep. 2006.
Glantschnig et al.; M-CSF, TNFalpha and RANK ligand promote osteoclast survival by signaling through mTOR/S6 kinase; Cell Death Differ; 10(10):1165-77; Oct. 2003.
Han et al.; TGFbeta1 selectively up-regulates CCR1 expression in primary murine astrocytes; Glia; 30(1):1-10; Mar. 2000.
Handelman; Nonsurgical rapid maxillary alveolar expansion in adults: a clinical evaluation; Angle Orthod; 67(4):291-305; Aug. 1997.
Haruyama et al.; Estrous-cycle-dependent variation in orthodontic tooth movement; J Dent Res; 81(6):406-410; Jun. 2002.
Hinton et al.; Upper airway pressures during breathing: a comparison of normal and nasally incompetent subjects with modeling studies; Am J Orthod; 89(6):492-498; Jun. 1986.
Hwang et al.; Intrusion of overerupted molars by corticotomy and magnets; Am J Orthod Dentofacial Orthop; 120(2):209-216; Aug. 2001.
Iino et al.; Acceleration of orthodontic tooth movement by alveolar corticotomy in the dog; Am J Orthod Dentofacial Orthop; 131(4):448.e1-e8; Apr. 2007.
Ito et al.; Augmentation of type I IL-1 receptor expression and IL-1 signaling by IL-6 and glucocorticoid in murine hepatocytes; J Immunol; 162(7):4260-4265; Apr. 1, 1999.
Jäger et al.; Soluble cytokine receptor treatment in experimental orthodontic tooth movement in the rat; Eur J Orthod; 27(1):1-11; Feb. 2005.
Jang et al.; Interleukin-18 gene polymorphisms in Korean patients with Behçet's disease; Clin Exp Rheumatol; 23(4 Suppl 38):S59-63; Jul.-Aug. 2005.

Kao et al.; Up-regulation of CC chemokine ligand 20 expression in human airway epithelium by IL-17 through a JAK-independent but MEK/NF-kappaB-dependent signaling pathway; J Immunol; 175(10):6676-6685; Nov. 15, 2005.
Kawasaki et al.; Effects of aging on RANKL and OPG levels in gingival crevicular fluid during orthodontic tooth movement; Orthod Craniofac Res; 9(3):137-142; Aug. 2006.
Khapli et al.; IL-3 acts directly on osteoclast precursors and irreversibly inhibits receptor activator of NF-kappa B ligand-induced osteoclast differentiation by diverting the cells to macrophage lineage; J Immunol; 171(1):142-151; Jul. 2003.
Khoo et al.; Accelerated Orthodontic Treatment; Dentista Y Pacienta; Mexican Dental Journal; Feb. 2011 edition; 11 pages total.
King et al.; Later orthodontic appliance reactivation stimulates immediate appearance of osteoclasts and linear tooth movement; Am J Orthod Dentofacial Orthop; 114(6):692-697; Dec. 1998.
King et al.; Measuring dental drift and orthodontic tooth movement in response to various initial forces in adult rats; Am J Orthod Dentofacial Orthop; 99(5):456-465; May 1991.
Kitaura et al.; An anti-c-Fms antibody inhibits orthodontic tooth movement; J Dent Res; 87(4):396-400; Apr. 2008.
Knüpfer et al.; sIL-6R: more than an agonist?; Immunol Cell Biol; 86(1):87-91; Jan. 2008.
Kole; Surgical operations on the alveolar ridge to correct occlusal abnormalities; Oral Surg Oral Med Oral Pathol; 12(5):515-529; May 1959.
Krishnan et al.; Cellular, molecular, and tissue-level reactions to orthodontic force; Am J Orthod Dentofacial Orthop; 129(4):469.e1-469.e32; Apr. 2006.
Krishnan et al.; On a path to unfolding the biological mechanisms of orthodontic tooth movement; J Dent Res; 88(7):597-608; Jul. 2009.
Lean et al.; CCL9/MIP-1gamma and its receptor CCR1 are the major chemokine ligand/receptor species expressed by osteoclasts; J Cell Biochem; 87(4):386-393; Sep. 2002.
Leng et al.; Interleukin-11; Int J Biochem Cell Biol; 29(8-9):1059-1062; Aug.-Sep. 1997.
Liou et al.; Rapid orthodontic tooth movement into newly distracted bone after mandibular distraction osteogenesis in a canine model; Am J Orthod Dentofacial Orthop; 117(4):391-398; Apr. 2000.
Luster; Chemokines—chemotactic cytokines that mediate inflammation; N Engl J Med; 338(7):436-445; Feb. 12, 1998.
McNamara et al.; Orthodontic and Orthopedic Treatment in the Mixed Dentition; Needham Press; pp. 131-144; Jun. 1993.
Meikle; The tissue, cellular, and molecular regulation of orthodontic tooth movement: 100 years after Carl Sandstedt; Eur J Orthod; 28(3):221-240; Jun. 2008.
Mermut et al.; Effects of interferon-gamma on bone remodeling during experimental tooth movement; Angle Orthod; 77(1):135-141; Jan. 2007.
Murphy; In Vivo Tissue Engineering for Orthodontists: A Modest First Step; Biological Mechanisms of Tooth Eruption, Resorption and Movement; Harvard Society for the Advancement of Orthodontics; pp. 385-410; Jan. 2006.
Piemonti et al.; Human pancreatic islets produce and secrete MCP-1/CCL2: relevance in human islet transplantation; Diabetes; 51(1):55-565; Jan. 2002.
Ren et al.; Cytokine profiles in crevicular fluid during orthodontic tooth movement of short and long durations; J Periodontol; 78(3):453-458; Mar. 2007.
Ren et al.; Cytokines in crevicular fluid and orthodontic tooth movement; Eur J Oral Sci; 116(2):89-97; Apr. 2008.
Rubin et al.; Inhibition of osteopenia by low magnitude, high-frequency mechanical stimuli; Drug Discov Today; 6(16):848-858; Aug. 16, 2001.
Rygh et al.; Activation of the vascular system: a main mediator of periodontal fiber remodeling in orthodontic tooth movement; Am J Orthod; 89(6):453-468; Jun. 1986.
Saito et al.; Interleukin 1 beta and prostaglandin E are involved in the response of periodontal cells to mechanical stress in vivo and in vitro; Am J Orthod Dentofacial Orthop; 99(3):226-240; Mar. 1991.

(56) References Cited

OTHER PUBLICATIONS

Sallusto et al.; Flexible programs of chemokine receptor expression on human polarized T helper 1 and 2 lymphocytes; J Exp Med; 187(6):875-883; Mar. 16, 1998.

Schneider et al.; Lymphotoxin and Light signaling pathways and target genes; Immunol Rev; 202:49-66; Dec. 2004.

Seidenberg et al.; Is there an inhibitory effect of COX-2 inhibitors on bone healing?; Pharmacol Res; 50(2):151-156; Aug. 2004.

Shih et al.; Regional acceleration of remodeling during healing of bone defects in beagles of various ages; Bone; 6(5):377-379; Feb. 1985.

Shireman; The chemokine system in arteriogenesis and hind limb ischemia; J Vasc Surg; 45 Suppl A:A48-A56; Jun. 2007 (Author's Manuscript).

Teixeira et al.; Cytokine Expression and Accelerated Tooth Movement; J Dent Res; 89(10):1135-1141; Oct. 2010.

Tran Ma; Method for studying the vascular region of bone; J Pharmacol; 13:495-499; Jul.-Sep. 1982 (in French).

Uematsu et al.; Interleukin (IL)-1 beta, IL-6, tumor necrosis factor-alpha, epidermal growth factor, and beta 2-microglobulin levels are elevated in gingival crevicular fluid during human orthodontic tooth movement; J Dent Res; 75(1):562-567; Jan. 1996.

Verna et al.; Histomorphometric study of bone reactions during orthodontic tooth movement in rats; Bone; 24(4):371-379; Apr. 1999.

Viazis, A; Atlas of Orthodontics: Principles and Clinical Applications; WB Saunders Co.; pp. 205-213; Apr. 1993.

Vignery et al.; Dynamic histomorphometry of alveolar bone remodeling in the adult rat; Anat Rec; 196(2):191-200; Feb. 1980.

Wilcko et al.; Rapid Orthodontic Decrowding with Alveolar Augmentation: Case Report; World J Orthod; 4(3):197-205; Sep.-Nov. 2003.

Wilcko et al.; Rapid orthodontics with alveolar reshaping: two case reports of decrowding; Int J Periodontics Restorative Dent; 21(1):9-19; Feb. 2001.

Williams et al.; Orthodontic tooth movement analysed by the Finite Element Method; Biomaterials; 5(6):347-351; Nov. 1984.

Xu et al.; Interleukin-18 promoter gene polymorphisms in Chinese patients with systemic lupus erythematosus: association with CC genotype at position -607; Ann Acad Med Singapore; 36(2):91-95; Feb. 2007.

Yaffe et al.; Regional accelerated phenomenon in the mandible following mucoperiosteal flap surgery; J Periodontol; 65(1):79-83; Jan. 1994.

Yamamoto et al.; Cytokine production in human periodontal ligament cells stimulated with Porphyromonas gingivalis; J Periodontal Res; 41(6):554-559; Dec. 2006.

Yao et al.; Osteoclast precursor interaction with bone matrix induces osteoclast formation directly by an interleukin-1-mediated autocrine mechanism; J Biol Chem; 283(15):9917-9924; Apr. 11, 2008.

Yen et al.; Closure of an unusually large palatal fistula in a cleft patient by bony transport and corticotomy-assisted expansion; J Oral Maxillofac Surg; 61(11):1346-1350; Nov. 2003.

Yoshimatsu et al.; Experimental model of tooth movement by orthodontic force in mice and its application to tumor necrosis factor receptor-deficient mice; J Bone Miner Metab; 24(1):20-27; Jan. 2006.

Zittermann et al.; Physiologic fluctuations of serum estradiol levels influence biochemical markers of bone resorption in young women; J Clin Endocrinol Metab; 85(1):95-101; Jan. 2000.

Way et al.; Design U.S. Appl. No. 29/497,897 entitled "Microperforation dental device," filed Jul. 29, 2014.

* cited by examiner

TEMPORARY ANCHORAGE DEVICE WITH EXTERNAL PLATE

RELATED APPLICATIONS

This application claims priority to U.S. Patent Application No. 61/656,776, filed Jun. 7, 2012, and titled "TEMPORARY ANCHORAGE DEVICE WITH EXTERNAL PLATE," the entirety of which is incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

In orthodontics, tooth movement generally requires placing force on the tooth, such as with braces. These forces require an anchoring point, such as a neighboring tooth. However, since the anchoring tooth is exposed to the same magnitude of reactive forces as the tooth or teeth being treated, the anchoring tooth often moves to an undesirable position. While these movements can be ignored for minor cases, in other cases, they can interfere with the orthodontic treatment. In extreme cases, the movements can require orthogenetic surgery, which has a relatively high morbidity rate, to replace the anchoring tooth.

To solve these problems, temporary anchorage devices (TADs) have been developed. These TADs are temporary implants that are placed in the jaw bone and can be connected an orthodontic device on the target tooth by springs or elastics. TADs can allow the target tooth to move in the desired direction while minimizing the effect on adjacent teeth.

Currently, there are two different designs for TADs. The first design is in the form of a single screw that is placed without surgery directly through the gum to the bone. However, this form of TAD, because it is a single screw, can be unstable and result in movement or dislodging of the screw during the anchoring process. Further, this type of screw mechanism traditionally has a screw thread extending the entire length of the device, which can both create irritation in the gums and provide a space for bacteria and other microorganisms to enter and cause infection.

The second TAD design includes an implantable surgical plate with multiple screws holding the external plate in place. This design must be implanted by a surgeon underneath the soft tissue such that the plate lies directly against the bone and is held in place with the screws. The surgical plate advantageously provides stability to the TAD. This design, however, requires the patient to undergo surgery, significant increasing the cost and risk associated with the design. Further, once implanted, the TAD cannot be adjusted or removed without further surgery. Moreover, if the external plate or the screws become loose over time, significant irritation can occur as a result of having the loose device in a closed space underneath the gums.

Accordingly, a TAD design that solves these problems is desired.

SUMMARY OF THE DISCLOSURE

The present invention relates generally to temporary anchorage devices.

In one embodiment, a temporary anchor device includes at least one screw mechanism and an external plate. The at least one screw mechanism includes a skeletal screw having a threaded portion configured to drill into jaw bone of a patient, a smooth portion configured to sit within gums of the patient, and a proximal portion configured to extend external to the gums. The at least one screw mechanism further includes an attachment mechanism configured to attach to the proximal portion of the skeletal screw. The external plate is configured to be locked between the skeletal screw and the attachment mechanism to anchor the external plate external to the gums.

In one embodiment, a method of anchoring an orthodontic device includes: screwing at least one skeletal screw through gums of a patient into jaw bone such that at least a proximal portion of the skeletal screw remains exposed external to the gums; placing an external plate on or around the proximal portion of the skeletal screw such that the external plate remains external to the gums; and attaching an attachment mechanism to the proximal end of the skeletal screw, thereby locking the external plate in place external to the gums.

These and other embodiments can include one or more of the following limitations.

The attachment mechanism can be configured to screw into the proximal portion of the skeletal screw.

There can be at least two skeletal screws. The external plate can include an elongate body having an elongate opening therein configured to fit the proximal portions of both screws therethrough.

The method can further include attaching an orthodontic device to the external plate.

The method can further include removing the attachment mechanism, removing the external plate, placing a second external plate on or around the proximal portion of the skeletal screw, and attaching the attachment mechanism to the proximal end of the screw, thereby locking the second external plate in place.

The external plate can include an orthodontic attachment feature configured to provide a point of attachment for an orthodontic device. The orthodontic device can include braces.

The smooth portion of the skeletal screw can be between 1-5 mm in length, such as approximately 3 mm. The helical portion can be between 2-10 mm in length, such as approximately 6 mm.

The method can further include placing the external plate such that it sits away from the gums, such as at least 0.5 mm, for example approximately 1 mm.

The orthodontic device can be placed near a posterior buccal plate of a maxillary or mandibular alveolar process. The orthodontic device can be placed such that it crosses a mid-palatal suture proximate to a first molar. The orthodontic device can be placed in an area of attached gingiva in an anterior buccal plate of a maxillary or mandibular alveolar process.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
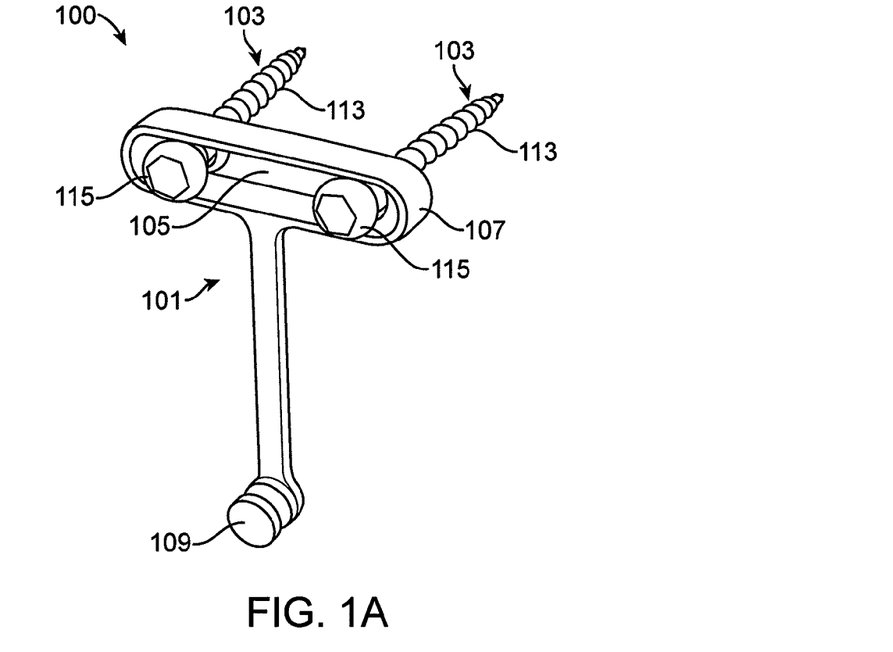
FIG. 1A is a front view of an exemplary temporary anchorage device as described herein.
Figure 1B:
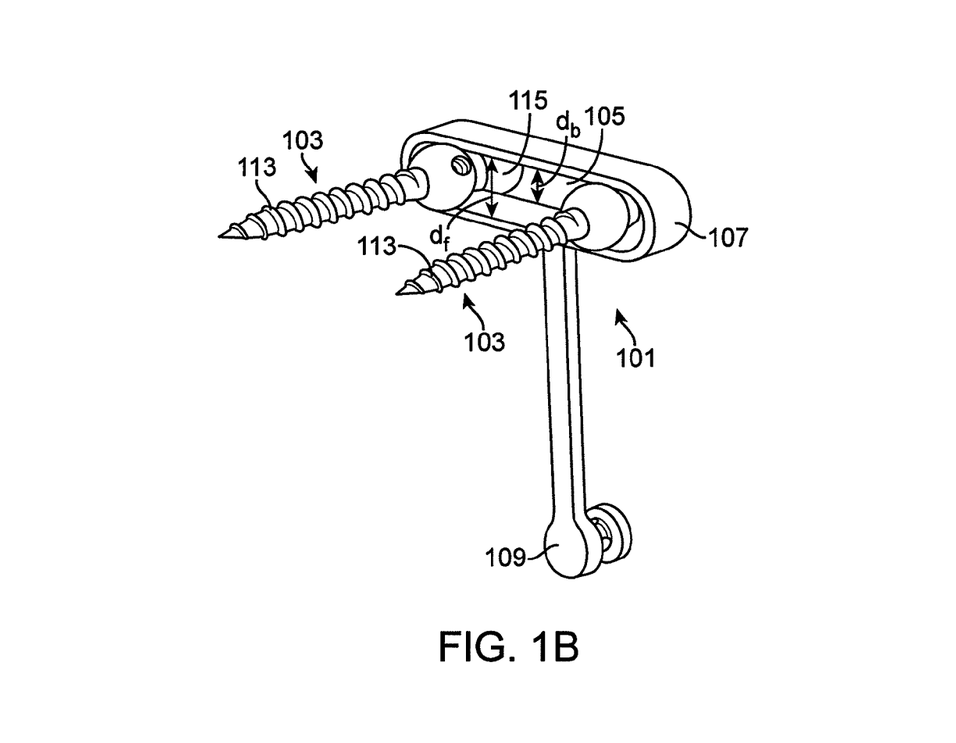
FIG. 1B is a back view of the exemplary temporary anchorage device of FIG. 1A.

Referring to FIGS. 1A and 1B, a temporary anchorage device (TAD) 100 includes an external plate 101. The external plate 101 includes an elongate body 107 having at least one hole 105 therein. In some embodiments, as shown in FIGS. 1A-1B, the external plate 101 further includes an orthodontic attachment feature 109, such as a button, configured such that an orthodontic device, e.g., braces, can be connected thereto. For example, a wire, elastic, or spring of the orthodontic device can be connected to the attachment feature 109. The TAD 100 further includes at least one screw mechanism 103 attached to the external plate 101. Each screw mechanism 103 can extend through the hole 105 of the external plate 101 to provide an anchoring mechanism for the external plate 101. Further, as discussed further below, each screw mechanism 103 can include two separate parts—a skeletal screw 113 and an attachment mechanism 115.

Figure 2A:
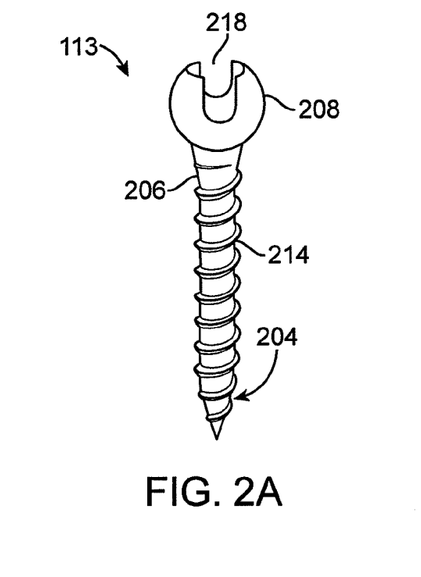
FIG. 2A shows the skeletal screw of the device of FIG. 1.
Figure 2B:
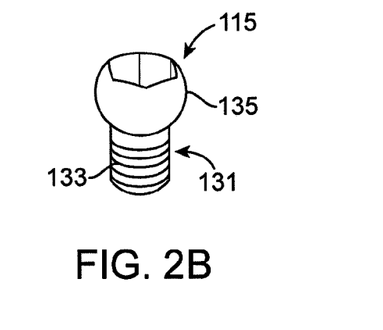
FIG. 2B shows the attachment mechanism of the device of FIG. 1.
Figure 2C:
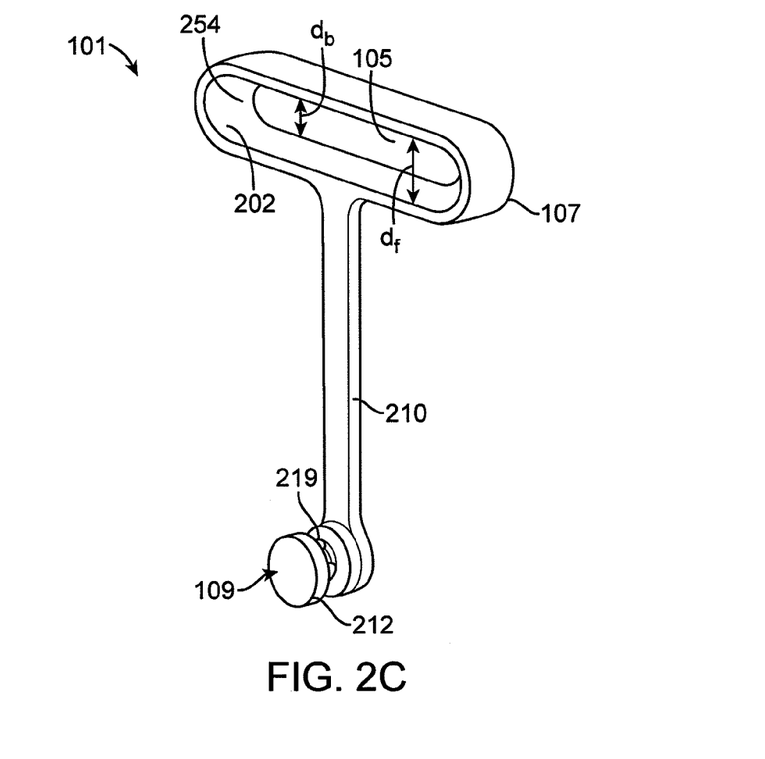
FIG. 2C shows the external plate of the device of FIG. 1.

The distinct parts of the TAD 100 are shown separately in FIGS. 2A-2C. As shown in FIG. 2A, the skeletal screw 113 includes a distal screw tip 204 having a helical thread 214 extending therearound. The skeletal screw 113 further includes a smooth middle portion 206, i.e. a portion without a thread. A proximal end 208 extends from the smooth middle portion 206. The proximal end 208 can have a diameter that is larger than the diameter of the middle portion 206. For example, the proximal end 208 can be bulbous or approximately spherical in shape. The proximal end 208 can further include a cut-out portion 218 configured to interlock with and/or hold the attachment mechanism 115 in place.

Referring to FIG. 2B, the attachment mechanism 115 can be configured to interlock with the proximal end 208 of the skeletal screw 113. For example, as shown in FIG. 2B, the attachment mechanism can include a screw-like portion 131 having threads 133 thereon configured to align with threads inside of the skeletal screw 113, such as inside the cut-out portion 218. Further, the attachment mechanism 115 can include a proximal end 135 configured to sit outside of the proximal end 135 of the skeletal screw 113 and hold the external plate 101 therebetween, as described further below.

As shown in FIG. 2C, the external plate 101 can include an elongate body 107 having at least one hole 105 therein. The hole 105 can run almost the entire length of the elongate body 107. By having an elongate body 107 and a hole 105 extending the length of the elongate body 107, the versatility of the TAD 100 and ease of implantation can be increased. Because the skeletal screw 113 of each screw mechanism 103 is implanted before the external plate 101, the elongated hole 105 can allow for simple placement of the external plate 101 over multiple skeletal screws 113. Accordingly, the elongated hole 105 allows for variation in the distance and angles between multiple skeletal screws 113. The elongate body 107 can further include sloped or beveled inner walls 202 leading from the front of the external plate 101 to the back of the external plate 101, i.e., the diameter $d_b$ of the hole 105 at the back of the elongate body 107 can be smaller than the diameter $d_f$ at the front of the elongate body 107. These sloped or beveled walls advantageously provide a ledge 254 or hook to lock the external plate 101 between the proximal end 208 (see FIG. 2A) of the skeletal screw 113 and the proximal end 135 (see FIG. 2B) of the attachment mechanism 115. That is, the proximal end 208 of the skeletal screw 113 and the proximal end 135 of the attachment mechanism 115 can both be too large to fit through the inner diameter of the hole 105, thereby forcing the two proximal ends 208, 135 to interact with the ledge 254.

As noted above, the external plate 101 can further include an orthodontic attachment feature 109 extending therefrom. For example, as shown in the FIG. 2C, the orthodontic attachment feature 109 can include an elongate extension portion 210 having a button 212 connected thereto. The button 212 can have an annular groove 219 therein configured to hold a wire or elastic of the orthodontic device. In some embodiments, the attachment feature 109 can be contiguous with and/or welded to the elongate body 107.

Figure 3A:
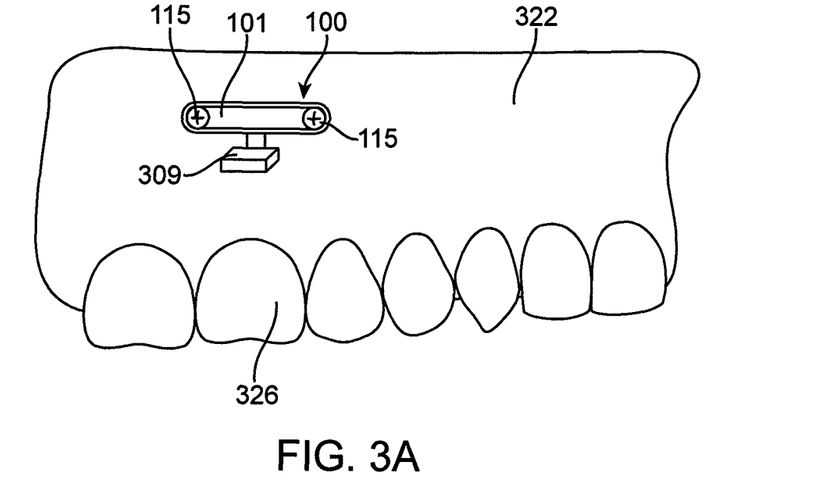
FIG. 3A shows a sagittal view of a temporary anchorage device placed in the jaw as described herein.
Figure 3B:
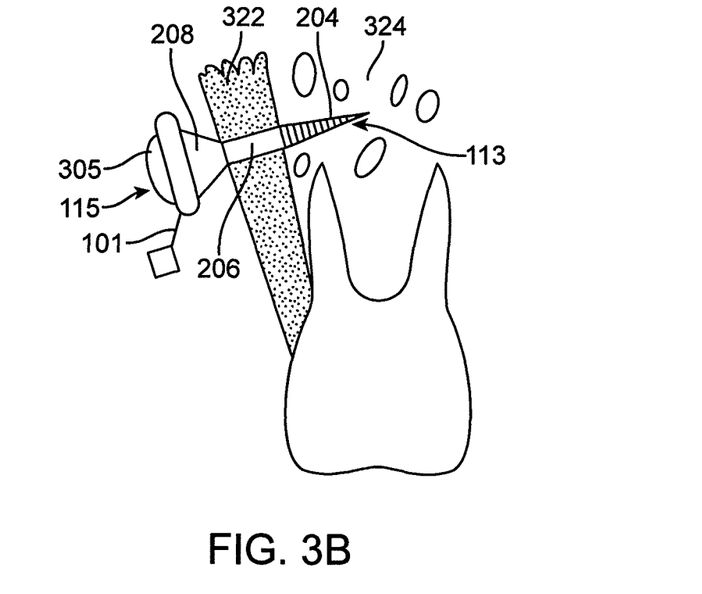
FIG. 3B shows a partially transparent frontal view of the temporary anchorage device placed in the jaw.

Referring to FIGS. 3A and 3B, the TAD 100 can be placed in the mouth of a patient such that the external plate 101 and at least a portion of the skeletal screw 113 and attachment mechanism 115 remain external to the gums 322 of a patient. In some embodiments, the orthodontic attachment feature 109 can extend towards the teeth 326 of the patient so as to provide a connection point for an orthodontic device. The TAD 100 can be placed, for example, into the posterior buccal plate of the maxillary and mandibular alveolar process or can be placed such that it crosses the mid-palatal suture in the area of the first molar. In other embodiments, such as for a TAD 100 having a relatively small external plate 101, the TAD 100 can be placed in the area of attached gingiva in the anterior buccal plate of maxillary and mandibular alveolar process. In some embodiments, the TAD 100 can be used without an external plate between the roots of any maxillary and mandibular teeth.

Figure 3C:
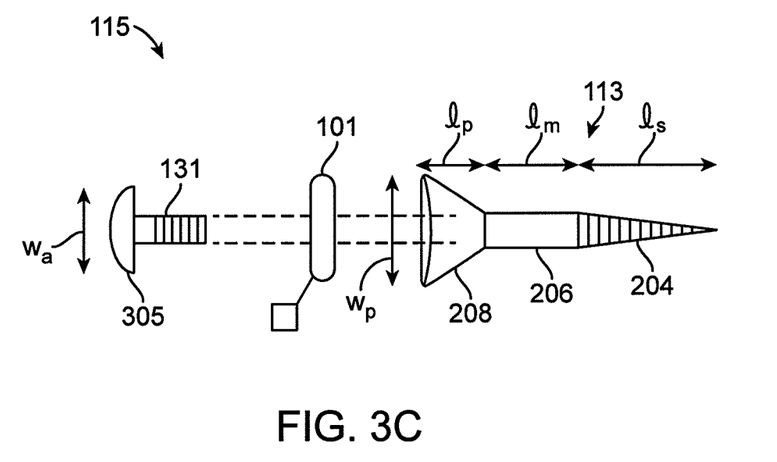
FIG. 3C shows the interlocking features of the TAD device when in use.

Referring to FIGS. 3B-3C, the TAD 100 can be placed by drilling the skeletal screw 113 into the jaws of the patient such that the screw tip 204 sits in the jaw bone 324 of the patient. Placing the screw tip 204 in the bone 342 of the patient advantageously provides a strong anchoring mechanism for the skeletal screw 113. Further, the skeletal screw 113 can be placed such that the smooth middle portion 206 sits within the gums 322 of the patient. The smooth middle portion 206 advantageously ensures that little irritation is caused to the gums 322 and/or reduces the probability of infection. The proximal end 208 of the skeletal screw 113 can sit external to the gums 322. The bulbous shape of the proximal end 208 can advantageously ensure that the proximal end of the skeletal screw 113 remains external to the gums 322. In some embodiments, one or more additional skeletal screws 113 are also placed through the gums 322 into the bone 324 of the patient.

Referring still to FIGS. 3B-3C, after the skeletal screw 113 has been set in place, the external plate 101 can be placed on or around the skeletal screw. For example, the external plate 101 can be placed such that at least a portion of the hole 105 extends over the proximal tip of the proximal end 208, i.e., through the diameter $d_f$ (see FIG. 2C). However, the diameter $d_b$ (see FIG. 2C) at the back of the elongate body 107 can prevent the proximal end 208 from extending all the way out through the hole 105 (see FIG. 1B). Accordingly, the proximal end 208 can sit against the inner side of the ledge 254 (see FIG. 2C) of the external plate 101. In some embodiments, if more than one skeletal screw 113 has been placed, the external plate 101 can be aligned such that it is placed on or around the additional skeletal screws as well.

Referring still to FIGS. 3B-3C, after the external plate 101 has been inserted over the skeletal screw or screws 113, the attachment mechanism 115 can be used to lock the external plate 101 in place. Thus, in one example, the screw portion 131 of the attachment mechanism 115 can be screwed into the skeletal screw 113, and the proximal end 135 of the attachment mechanism 115 can sit against the outer side of the ledge 254 (see FIG. 2C). That is, the diameter of the proximal end 135 can be such that it is too large to fit through the diameter $d_f$ of the hole 105 (see FIG. 1B). If multiple skeletal screws 113 have been placed, then additional attachment mechanisms 115 can be placed accordingly. As a result, the external plate 101 can be locked into placed outside of the gums 322 of the patient. In some embodiments, the external plate 101 is held away from the gums of the patient to prevent irritation of the gums 322, such as with the proximal portion 208 of the skeletal screw 113. For example, the external plate 101 can sit at least 0.5 mm away from the gums 322, such as approximately 1 mm away from the gums. Keeping the external plate away from the gums reduces irritation and provides easy access for cleaning around the TAD 100.

The external plate 101 can advantageously be removed and replaced with a different external plate during use. That is, the attachment mechanism 115 can be removed, the external plate 101 removed, and then a new external plate locked into place with the attachment mechanism 115. By allowing the external plate 101 to be removable, the same screw mechanisms 103 can be used to support a variety of different external plates. Accordingly, the external plate can be changed, e.g., to switch to a different size or shape, easily without the need for surgery.

In some embodiments, a single screw mechanism 103 can be placed, used as a single attachment for a small external plate, and then additional screw mechanisms 103 can be placed at a later time for use with larger or different external plates. This step-by-step process can advantageously avoid unnecessary trauma in a single setting, particularly for small children.

Referring back to FIG. 3C, the dimensions of the screw mechanism 103 can be chosen so as to seat the screw mechanism 103 properly in the jaws and gums. For example, the length (ls) of the screw tip 204 can be between 2 mm and 10 mm, such as approximately 6 mm. This length can advantageously ensure that the screw tip 204 is well anchored while ensuring that as little damage as possible is done to the bone and that the screw mechanism 103 can be placed efficiently. Further, the length (lm) of the smooth middle portion 206 can be between 1 mm and 4 mm, such as approximately 3 mm. This length can correspond approximately to the width of the gums. Further, the proximal end 208 can have a length (lp) and/or width (wp) of 1-3 mm, such as approximately 2 mm. The width (wa) of the proximal end 135 of the attachment mechanism 115 can likewise be 1-3 mm, such as approximately 2 mm.

After the TAD device 100 has been placed in the patient, it can be used to anchor an orthodontic device. Accordingly, the TAD device 100 can be used, for example, for correction of severe open bite, retraction of anterior teeth, correction of mandibular prognatism, correction of maxillary prognatism, correction of severe anterior cross bite, intrusion of single or multiple teeth, correction of posterior cross bite, protraction of posterior teeth, and/or correction of deep bite.

Although the TAD 100 has been described as including a particular type of external plate 101, other variations are possible. For example, the walls 202 could be sloped in the opposite direction such that the diameter of the front of the hole 105 is larger than the diameter of the back of the hole 105. Further, the external plate need not be in the shape shown in FIGS. 1, 2, and 3, but could take other shapes. Likewise, the size and shape of the orthodontic attachment feature 109 could vary.

Figure 4A:
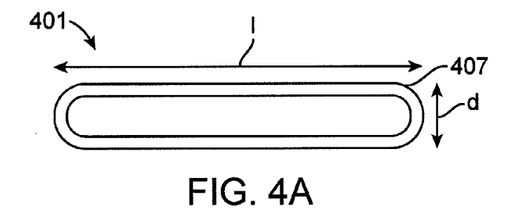
FIG. 4A shows a sagittal view of an exemplary external plate.
Figure 4B:
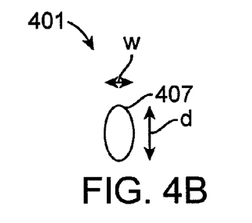
FIG. 4B shows a frontal view of the external plate of FIG. 4A.

For example, referring to FIGS. 4A and 4B, the external plate 401 could have an elongate body 407 without an extending orthodontic attachment feature. The external plate 401 can be available in different sizes, ranging from 6 mm to 15 mm in length (l), such as approximately 8 mm, 10 mm, or 12 mm. The width (w) can be between 0.5 and 3 mm, such as approximately 1 mm. Further, the depth d can be between 1 mm and 5 mm, such as approximately 2 mm.

Figure 5A:
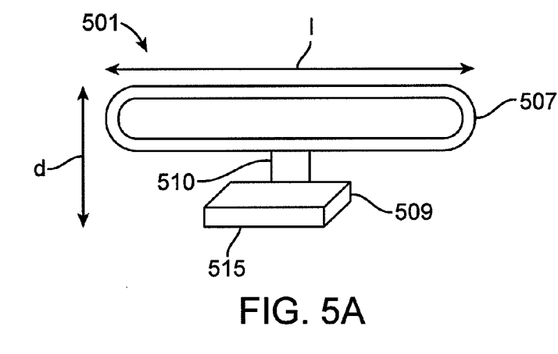
FIG. 5A shows a sagittal view of another embodiment of an exemplary external plate.
Figure 5B:
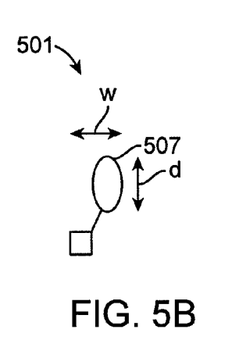
FIG. 5B shows a frontal view of the external plate of FIG. 5A.

Referring to FIGS. 5A and 5B, the external plate 501 can include an elongate body 507, similar to the elongate body 407 described with respect to FIG. 4. However, the external plate 501 can further include an orthodontic attachment feature 509 extending from the elongate body 507. The orthodontic attachment feature 509 can include an elongate extension portion 510 and a molar tube 515 attached thereto. The molar tube 515 can be configured such that a wire can be passed therethrough. For example, the molar tube can be a rectangular tube, such as a standard edgewise tube without angulation. The elongate extension portion 410 can be curved such that the molar tube 515 is extends out and away from the elongate body 507 and/or the gums, as shown in FIG. 5B. Keeping the molar tube 515 away from the gums advantageously decreases irritation to the gums of the patient. Thus, the total width (w) of the external plate 501 can be between 1 mm and 5 mm, such as approximately 3 mm. Further, the extension portion 510 and the molar tube 515 can add between 1 mm and 10 mm to the depth (d), such as approximately 4 mm.

Figure 6A:
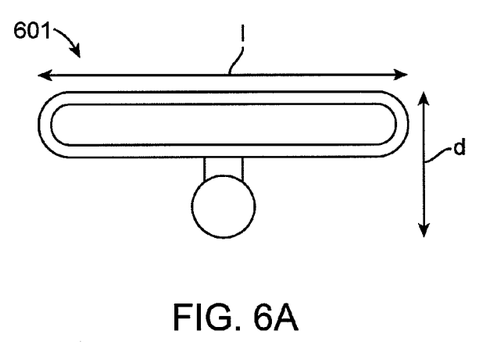
FIG. 6A shows a sagittal view of another embodiment of an exemplary external plate.
Figure 6B:
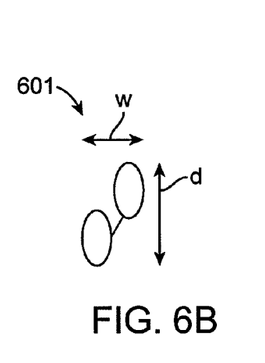
FIG. 6B shows a frontal view of the external plate of FIG. 6A.

Referring to FIGS. 6A and 6B, the external plate 601 can be similar to the external plate 501 except that it can include a round button 517 in place of the molar tube 515. The round button can be used, for example, to connect spring or elastics from braces. For example, the button can include a groove and/or necked portion that allows a power chain or elastic to be connected thereto.

Figure 7A:
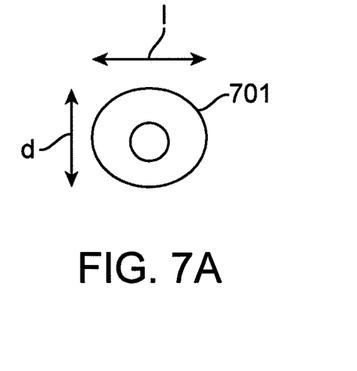
FIG. 7A shows a sagittal view of another embodiment of an exemplary external plate.
Figure 7B:
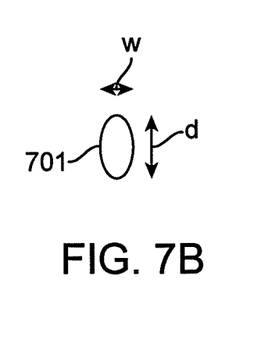
FIG. 7B shows a frontal view of the external plate of FIG. 7A.

Further, the external plate need not include an elongate body at all, but could be relatively small and configured to attach to a single screw 103. For example, the external plate could be just small enough to fit a single screw mechanism therethrough, such as the round plate 701. The round plate 701 can advantageously increase the bulk of the head of the screw such that an elastic or wire can be attached behind the round plate 701. The round plate 701 can have a depth (d) and/or length (l) of 1-5 mm, such as approximately 3 mm and a width (w) of 0.5 to 3 mm such as approximately 1 mm.

Figure 8A:
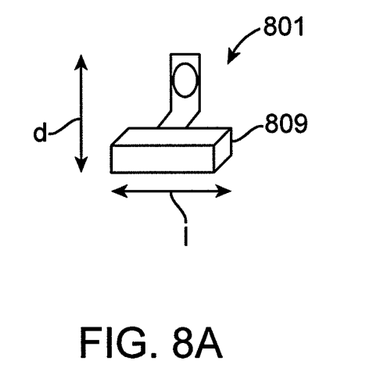
FIG. 8A shows a sagittal view of another embodiment of an exemplary external plate.
Figure 8B:
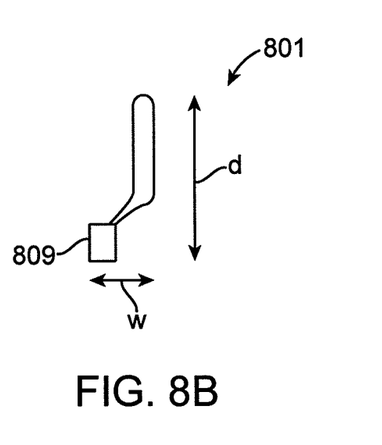
FIG. 8B shows a frontal view of the bite plate of FIG. 8A.

Similarly, as shown in FIGS. 8A and 8B, the external plate 801 could be a small square device with a hole therethrough only large enough to fit a single screw mechanism and include an orthodontic attachment mechanism 809. The plate 801 can have a depth (d) of 1-6 mm, such as approximately 4 mm, a length (l) of 1-5 mm, such as approximately 3 mm, and a width (w) of 1-3 mm, such as approximately 2 mm.

Advantageously, the TAD described herein can be placed, removed, and adjusted without the need for a surgical procedure. Further, the TAD described herein can be advantageously stable due to the use of an external plate supported by multiple screws, i.e., having multiple screws can both divide the between the screws to avoid overloading a single screw and balance the moments across the various screws. Moreover, because no surgery is required, the TAD described herein is advantageously affordable for the patient and can be placed and in a short period of time, such as a few minutes, with very few side effects.

What is claimed is:

1. A temporary anchorage device comprising:
at least one screw mechanism, the screw mechanism including:
a skeletal screw having a threaded portion configured to drill into jaw bone of a patient, a smooth portion having a length between 1-5 mm and configured to sit within gums of the patient, and a proximal portion configured to extend external to the gums;
an attachment mechanism configured to attach to the proximal portion of the skeletal screw; and
an external plate configured to be locked between the skeletal screw and the attachment mechanism to anchor the external plate external to the gums.

2. The temporary anchorage device of claim 1, wherein the attachment mechanism is a screw configured to screw into the proximal portion of the skeletal screw.

3. The temporary anchorage device of claim 1, wherein there are at least two skeletal screws.

4. The temporary anchorage device of claim 3, wherein the external plate comprises an elongate body having an elongate opening therein configured to fit the proximal portions of both screws therethrough, wherein the elongate body further comprises beveled inner walls leading from a front of the external plate to a back of the external plate.

5. The temporary anchorage device of claim 1, wherein the external plate comprises an orthodontic attachment feature configured to provide a point of attachment for an orthodontic device.

6. The temporary anchorage device of claim 5, wherein the orthodontic device comprises braces.

7. The temporary anchorage device of claim 1, wherein the smooth portion of the skeletal screw is approximately 3 mm in length.

8. The temporary anchorage device of claim 1, wherein the helical portion is between 2-10 mm in length.

9. The temporary anchorage device of claim 1, wherein the helical portion is approximately 6 mm in length.

10. A method of anchoring an orthodontic device comprising:
screwing at least one skeletal screw through gums of a patient into jaw bone such that at least a proximal portion of the skeletal screw remains exposed external to the gums and a smooth portion having a length of between 1-5 mm sits within the gums;
placing an external plate on or around the proximal portion of the skeletal screw such that the external plate remains external to the gums; and
attaching an attachment mechanism to the proximal end of the skeletal screw, thereby locking the external plate in place external to the gums.

11. The method of claim 10, further comprising attaching an orthodontic device to the external plate.

12. The method of claim 10, further comprising removing the attachment mechanism, removing the external plate, placing a second external plate on or around the proximal portion of the skeletal screw, and attaching the attachment mechanism to the proximal end of the screw, thereby locking the second external plate in place.

13. The method of claim 10, further comprising placing the external plate such that it sits a distance away from the gums.

14. The method of claim 13, wherein the distance is at least 0.5 mm.

15. The method of claim 13, wherein the distance is approximately 1 mm.

16. The method of claim 10, wherein the orthodontic device is placed near a posterior buccal plate of a maxillary or mandibular alveolar process.

17. The method of claim 10, wherein the orthodontic device is placed such that it crosses a mid-palatal suture proximate to a first molar.

18. The method of claim 10, wherein the orthodontic device is placed in an area of attached gingiva in an anterior buccal plate of a maxillary or mandibular alveolar process.

* * * * *